United States Patent
Blake

Patent Number: 6,035,854
Date of Patent: Mar. 14, 2000

[54] ABBREVIATED CONDOM WITH CLEFT WEDGE

[76] Inventor: Rory P. Blake, 3216 Chaucer Dr., Charlotte, N.C. 28210

[21] Appl. No.: 09/294,021

[22] Filed: Apr. 20, 1999

[51] Int. Cl.$^7$ .................................................. A61F 6/04
[52] U.S. Cl. ........................ 128/844; 604/349; 604/352; 128/842; 128/843
[58] Field of Search .................................. 604/349, 352; 128/842, 843, 844

[56] References Cited

U.S. PATENT DOCUMENTS 4,869,269  9/1989  Sharkan .

Primary Examiner—John G. Weiss
Assistant Examiner—Kevin Hart

[57] ABSTRACT

Securement of a condom to the glans penis is facilitated by a molded, contoured, or thickened wedge portion which fits snugly within the cleft of the glans such that a continuous circumferential seal may be obtained about the glans penis. An expansible seminal reservoir is provided and the shaft of the penis, as well as the rear portion of the glans penis opposed to the cleft, may be left unsheathed in order to allow greater sensitivity. A greater wall thickness than that typically utilized in a full length condom may be used without significant loss of sensitivity and a stronger condom more resistant to tearing during use than a conventional full length latex condom is obtained. An adhesive backing with a tab allows location of the device prior removal of the backing to ensure correct positioning and an effective circumferential seal with the adhesive. Regardless of whether or not the entire corona of the glans is encompassed a wedge shaped structure fitting in the cleft between the two lobes of the glans is utilized to obtain an anatomically accurate interior annular surface which is recommended for bearing an adhesive layer though an elastic band may be utilized in the case the entire corona is encompassed.

19 Claims, 3 Drawing Sheets

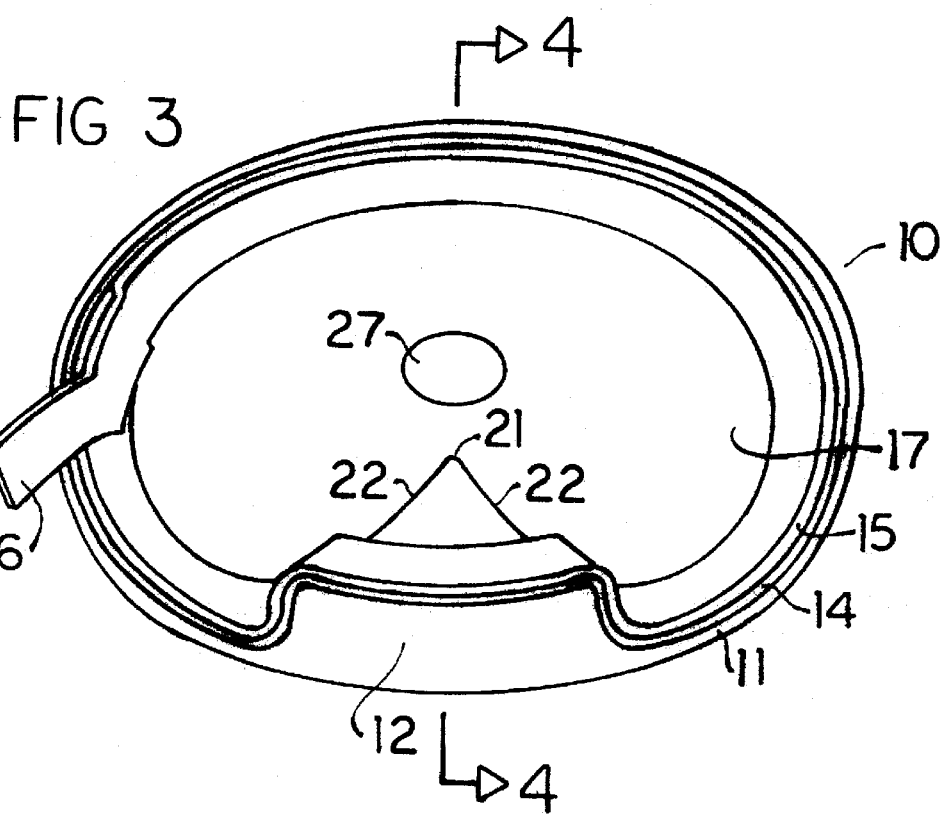
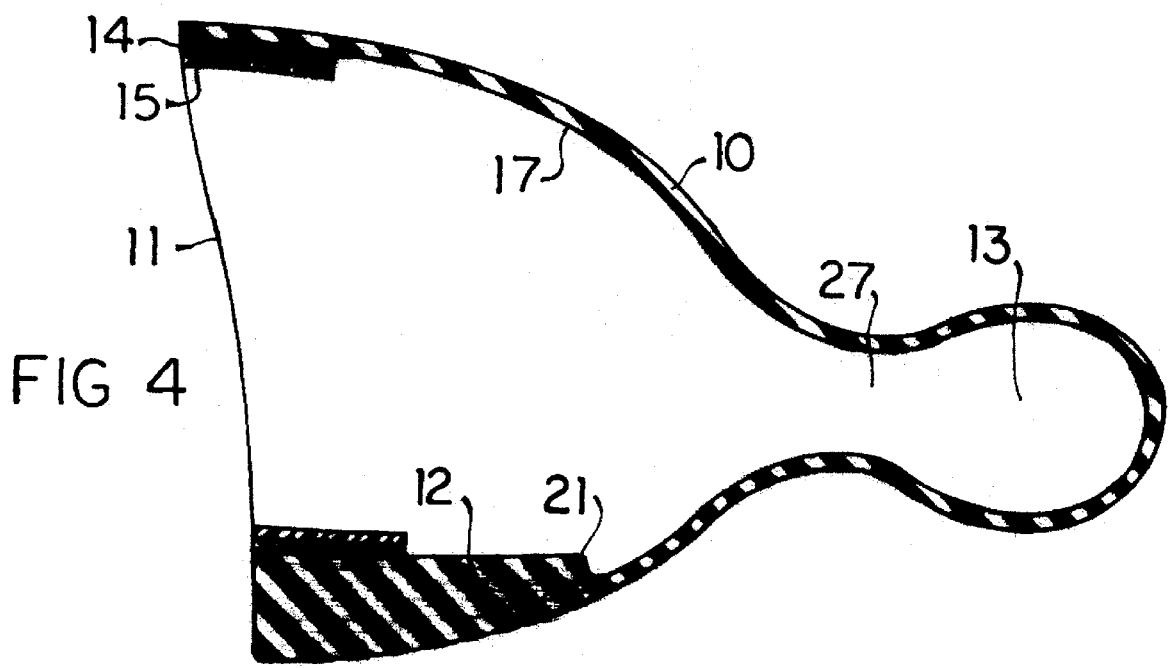

ABBREVIATED CONDOM WITH CLEFT WEDGE

BACKGROUND OF THE INVENTION

1. Field of the Invention

The general field of the present invention relates to condoms, i.e. prophylactic sheaths, and more particularly to condoms which are of abbreviated length which cover only the glans penis during use.

2. General Background

Condoms have traditionally served as a means of prophylaxis against conception. More recently, with the development of birth control pills and the increase in contagion of various sexually transmitted diseases, (STDs), condoms have become valued more, perhaps, as a means of prophylaxis against transmission of STDs than against conception. Several aspects regarding the use of condoms as opposed to other forms of preventing conception are recognized. Condoms are known to break during use and other forms of preventing conception, primarily birth control pills, are generally considered to be at least as effective as a condom for preventing conception.

The woman, moreover, possesses an assurance in knowing she is relatively safe from pregnancy if she is taking birth control pills regularly. A condom may break during use and while the man may readily discern this condition the woman cannot. A man might ignore the breakage or be truly unaware of the same and in either case the woman is typically without recourse to remedy the situation in which she has the more direct interest. The presence of a conventional full length latex condom essentially is not noticed by a female during intercourse but the same drastically reduces the sensitivity of the penis and the pleasure derived from the same activity for males who consequently frequently dislike wearing condoms for this reason. It is considered that the male aversion to wearing of a conventional full length latex condom was and is still a major factor in the adoption of alternative birth control measures by women.

In addition to birth control pills, interuterine devices, (IUDs), diaphragms and spermicidal jelly have been widely popular as alternatives to condoms for the prevention of unwanted pregnancies. The popularity of these measures is considered in view of the disadvantages associated with each. Birth control pills alter the body's chemistry and although the levels of estrogen and progestogen utilized has been decreased over the last several decades of use the fact remains that side effects attend regular and particularly regular and prolonged use of birth control pills. IUDs have been associated with serious medical problems for various reasons and many women generally find the implantation of the devices to be objectionable and the presence of the devices to be a marked source of discomfort. The use of diaphragms and spermicidal jelly poses a considerable inconvenience upon the woman as insertion is often difficult and the required presence of the device for many hours after intercourse is often uncomfortable. However, despite all these inconveniences, all three methods have been and are still quite popular as an alternative to the use of conventional condoms which pose neither inconvenience nor discomfort nor threat of physical side effects to the woman other than the reliance upon the willing cooperation of the male including detection of the breaking and prompt replacement of a broken condom during use.

In essence it is considered that, for the purposes of preventing unwanted pregnancy, many forms of contraception are preferred as alternatives to the use of a conventional full length latex condom by women despite the discomfort and risks associated with these alternatives because men dislike wearing conventional full length latex condoms and can not be reliably expected to use the same in a responsible manner simply because of the adverse affect upon the sensitivity of the penis imposed by the wearing of this prophylactic sheath. Most recently, approval has been granted for the marketing of a "morning after" birth control pill which will enable women to prevent contraception hours after coitus, hence practically removing any inhibition against having intercourse imposed by the adoption of a prophylaxis against an unwanted pregnancy.

However, there is no known alternative to a prophylactic device worn by the male for the prevention of infection by STDs during coitus. A conventional full length latex condom is widely recognized as the only effective means of avoiding STD contagion during coitus and is generally considered effective in protecting the male as well as the female from contacting a STD from the other during intercourse. The transmission of a disease from a male to a female during coitus is considered mainly to be associated with transfer of seminal fluid. More specifically, it is the absorption of the seminal fluid by mucous membranes such as that which line the vagina, which is considered to result in the sexual transmission of a disease from a male to a female during coitus. A regards the reverse process, i.e. the transmission of disease from the female to the male during coitus, it is considered that for a healthy, epidermally unbroken, penis only the urethra provides a mucous membrane lining which is susceptible to infection but without a condom this avenue of infection is quite adequate for the acquisition of a STD by the male.

In short, it is recognized that men dislike wearing conventional full length condoms because of the loss of sensitivity which results, and if the avoidance of pregnancy is the only concern there are other contraceptive alternatives to the use of a condom by the man which the woman may adopt, however, only a condom is considered effective in preventing the transmission of disease during coitus. Therefore, despite the many various advances in contraceptives over the last several decades touched upon above, relatively recent condom development, as evidenced by the number of U.S. Patents issued annually for the same, accelerated markedly in response to the increase in STDs during the last fifteen years in the United States. This recent development, as discussed below, includes consideration of an abbreviated condom which would not greatly diminish sensitivity and hence would be less objectionable to use by the male. As discussed at some length above, the loss of sensitivity imposed by wearing of a conventional full length latex condom is considered central to the common male aversion to proper use of the same and this aversion is considered to be the main reason the risk of acquiring a STD is tolerated by both men and women.

3. Discussion of the Prior Art

U.S. Pat. No. 2,703,574 issued to A. Hirschfeld Mar. 8, 1955 discloses a 'Rubber Sanitary Device' or abbreviated condom intended to enclose the glans penis and be held in place by a bottom thickened ring or band intended to seal the device "in engagement with the posterior annular portion of the glans" (Col. 1, Lines 60–62); the remainder of the device being of generally sufficient proportion to accommodate the anticipated seminal fluid.

U.S. Pat. No. 2,816,542 issued to R. B. Freeman Dec. 17, 1957 for a 'Prophylactic Tube With Differential Wall Thickness' discloses a singular convex, semi-spherical, and oblate projection or thickening of a full length condom intended for location below the anterior cleft of the glans in order to diminish stimulation of what is considered a particularly sensitive area in order to delay climax.

U.S. Pat. No. 4,820,290 issued to James H. Yahr Apr. 11, 1989 for a 'Prophylactic Device' discloses an abbreviated condom intended to enclose the glans penis, being held in place by a thickened band "to be positioned in the coronal sulcus to prevent leakage of fluids collected in the hood" (Abstract) which has a double wall, the interior wall being open internally for egress of the fluid.

U.S. Pat. No. 4,821,742 issued to John Y. Phelps, III Apr. 18, 1989 for a 'Contraceptive Device' discloses an abbreviated condom intended to fit upon the glans penis above the corona and held in place by adhesive interrupted in areas central and extending radially downward from the top of the device.

U.S. Pat. No. 4,869,269 issued to Arnold L. Sharkan for a 'Contraceptive Device: Micro-Condom' discloses use of "medical grade adhesive" to form "a leak-free seal with the" glans penis which "eliminates the need for the roll-down hood" and which increases "user pleasure" and whereby "the breakage problem" may be "solved with thicker material" (Abstract) and which further discloses an indenture 15 "in the frusto-conical portion 14 to correspond approximately the indenture in the underside of the" glans penis (Column 3, Lines 22–24).

DT 25 19 357 issued to A. Kopelowicz Nov. 11, 1976 for an 'Elastic Cap Contraceptive Sheath discloses an abbreviated condom for enclosing the glans penis possessing "concertina folds" (English Abstract) above the center top of the device which is held in place by a bottom adhesive band which folds over after location of the device.

CA 2034764-A issued to Richard Sauvé24 Jul. 1992 for a 'Condom For Protection During Sex' discloses an abbreviated condom intended to enclose the glans penis, being held in place by a thickened band below the glans having a expansible receptacle on the top folded flat prior ejaculation.

U.S. Pat. No. 5,421,350 issued to Leah Friedman Jun. 6, 1995 for a 'Condom Having Adhesive Means' discloses an abbreviated condom which is angled for a better fit over the glans penis to which it is secured by both a bottom annular reinforcement and adhesive, a reservoir at the top being also provided for seminal fluid.

U.S. Pat. No. 5,458,114 issued Oct. 17, 1995 to Jan E. Herr for a 'Contraceptive Penile Cap' discloses a bowl shaped structure with a central aperture held onto the glans with "medical grade adhesive" and possessing a "collapsed bladder contained within a protective retaining structure" into which the semen flows whereby the "sensitive corona of the glans is left exposed" (Abstract).

Statement of Need

The prior art discussed above demonstrates a variety of abbreviated condoms fitting either around the glans or attached with adhesive thereto. In particular, it is noted that a number of aspects may be recognized in the attempt to achieve satisfactory attachment to the glans only have been disclosed in the prior art: use of a band below the corona or ridge of the glans penis; use of adhesive; use of a band below the corona on an angled shape together with use of adhesive; use of a collapsible reservoir; and use of an indenture in what is otherwise a frusto-conical shape. In all such cases the condom is attached to a portion of the glans and the shaft of the penis is left exposed.

As essentially demonstrated by the variety of approaches chronicled above in the pertinent prior art, it is considered that the central problem of obtaining a secure attachment of such a device with a sufficient reservoir which possesses effective resistance to accidental displacement as well as breakage has not been solved and that therefore a need still exists for an abbreviated condom which will reliably protect against an exchange of seminal fluid while leaving most of the penis exposed. In particular, it is considered that the prior art fails to disclose a structure which will ensure an effective seal against leakage of seminal fluid in attachment to the glans penis.

SUMMARY OF THE INVENTION

Objects of the Invention

The encompassing object of the principles relating to the present invention is the provision of a condom of abbreviated length which attaches to the glans penis, leaving the shaft of the penis exposed, which possesses a structure that conforms anatomically to the glans penis about a circumference of the same whereby a continuous adhesive seal may be obtained in retention of seminal fluid and securement of the condom.

An auxiliary object of the principles relating to the present invention is the provision of a condom of abbreviated length which possesses a structure that includes a wedge shaped portion projecting inwardly which conforms anatomically to the cleft between the two glans of the glans penis in order to achieve a continuous adhesive seal about the circumference of the glans penis.

Another auxiliary object of the principles relating to the present invention is the provision of a condom of abbreviated length which possesses a band of adhesive disposed upon an interior surface that includes a wedge shaped portion projecting inwardly which conforms anatomically to the cleft in order to achieve a continuous seal about the circumference of the glans penis which has a removable backing with a tab which facilitates removal of the backing after location of the device.

An ancillary object of the principles relating to the present invention is the provision of a condom of abbreviated length which possesses a structure that conforms anatomically to the glans penis about a circumference of the same whereby a continuous adhesive seal may be obtained and in which retention of seminal fluid is facilitated by an expansible reservoir disposed substantially flush with the glans penis prior ejaculation.

Other ancillary objects of the principles relating to the present invention include the provision of a condom of abbreviated length of durable and preferably inexpensive construction which is less prone to accidental breakage than a conventional condom.

Principles Relating to the Present Invention

As may be discerned in the statement of the objects of the present invention above, an abbreviated, i.e. short, condom in accordance with the principles relating to the present invention obtains an effective seal of the glans penis, i.e. the head of a penis, with use of an anatomically accurate shape which includes any structure which 'bridges' or conforms with the structure of the cleft between the glans. It is first considered that the cleft extends from a point proximate the opening of the urethra, or forward end of the penis, rearward and outward defining the under side of the corona, i.e. the ridge of the glans. Secondly, it is also considered that the glans, apart from being bifurcated by the cleft ventrally, i.e. on the bottom, is also much larger dorsally with a wide, solid, structure diametrically opposed to the cleft. The terms 'ventral' and 'dorsal' are considered further. The former derives from the Latin for one's belly, the latter from the Latin for one's back. Apart from connoting the belly or underside and the back or upper side of a person or an animal the terms ventral and dorsal also are used to connote the underside and upper side, respectively, of an organ.

It is this sense of these terms which is utilized herein with the ventral portion of the head of a penis characterized by the cleft between the glans. It is further observed that the head of a penis is bilaterally symmetric with regard to a first nominally vertical plane with a second nominally horizontal plane normal to a first plane defining ventral and dorsal portions. The two planes intersect along an nominally horizontal axis substantively coincident with the urethra which is taken to be horizontal for purposes of the nomenclature utilized herein. A division into quadrants is obtained wherein it is observed that the dorsal or upper two quadrants comprise the bulk of the structure of the glans penis and that this dorsal half extends much further back from the forward end of the penis than does the ventral half. The sense of the word 'dorsal' in connoting the back is hence considered descriptive of the anatomy concerned as opposed to the ventral portion with regard to forward and backward as well as lower and upper surfaces because the rearward portion is comprised by the dorsal portion.

It is considered that the cleft between the glans terminates within proximity of the forward opening of the urethra and that the ridge of the glans penis, i.e. the corona, possesses an incline upward from the forward termination rearward and that this incline is approximately forty-five degrees using the urethra as a horizontal axis as described above. This means that the bifurcated rearward edges of the corona ventrally are forward of the rearward edge of the corona dorsally by a distance approximately equal to the vertical height of the organ. The corona, moreover, defines a complex curve which, though bilaterally symmetric, varies radially and while generally diminishing in radius from the dorsal rear edge to the ventral front termination, also defines bilateral symmetric lobes at the forward end with the cleft comprising the space between these two lobes.

The cleft widens rapidly rearward of these two lobes and is therefore bounded at the forward end only by what is described as bilaterally symmetric complex convex surfaces as largely determined by the shape of the two lobes characterizing the forward and ventral portion of the glans penis. While these two lobes substantially merge a small distance rearward from the urethra opening, a superficial division between the lobes is still clearly seen to extend forward of this substantive merging into the vertical slot comprising the urethra opening. This is opposed to the dorsal portion of the glans penis which is bilaterally symmetric but wholly lacking in any bifurcation.

It is considered that while the corona may be utilized to maintain the position of an abbreviated condom, particularly with the use of a thickened band or ring, a failure to provide structure which will conform to the anatomy of the bilaterally lobed ventral portion of the glans penis including the cleft therebetween will be problematic. More specifically it is considered that the provision of structure which enables conformance to the bilaterally lobed ventral portion of the glans penis is essential to achieving an abbreviated condom which will reliably contain seminal fluid. It is considered that a structure conforming to these bilateral lobes preferably possesses a pair of concave interiorly stepped surfaces which extend rearward from a common juncture.

The circumferential edge is further preferably curved to conform to the peripheral radius of the corona where the same is transversed and the degree of interior stepping preferably reflects the difference in radial distance from an axis substantively coincident with the urethra between the ventral glans and the cleft.

The efficacy of this structure is considered with regard to three cases which serve as boundary conditions considered to be determinative in the construction of an abbreviated condom in accordance with the principles relating to the present invention. In the first case the structure conforming to the bilateral lobes characterizing the ventral portion of the glans penis might be solid and comprise, essentially, an interiorly projecting protrusion to the condom. In the second and third cases, which are both opposed to the first, said structure conforming to the bilateral lobes characterizing the ventral portion of the glans penis might be substantively vacant with simple conformance to the contours of the cleft, either as a hollow or a double walled structure which may serve as a primary or secondary seminal fluid reservoir, or simply comprising a void exterior to the condom. This third case may also provide for a primary or secondary seminal fluid reservoir in being of expansible construction.

In all cases it is additionally recommended that medical grade adhesive be utilized to obtain both securement of disposition of the abbreviated condom and a seal against loss of seminal fluid. With regard to location and securement of the abbreviated condom in accordance with the principles relating to the present invention it is further considered that the structure conforming to the bilateral lobes characterizing the ventral portion of the glans penis is inherently facilitative of an intuitive positioning upon the head of the penis and that a strip of backing for the adhesive may be utilized which is removable after positioning has been satisfactorily achieved in order to ensure that a proper seal is obtained and is not compromised by displacement after adhesion is effected.

BRIEF DESCRIPTION OF THE DRAWINGS

FIG. 3 is a plain elevational view taken from the back of a first preferred embodiment of the principles relating to the present invention.

FIG. 4 is a cross sectional view taken from FIG. 3.

DETAILED DESCRIPTION OF THE PREFERRED EMBODIMENTS

Figure 1:
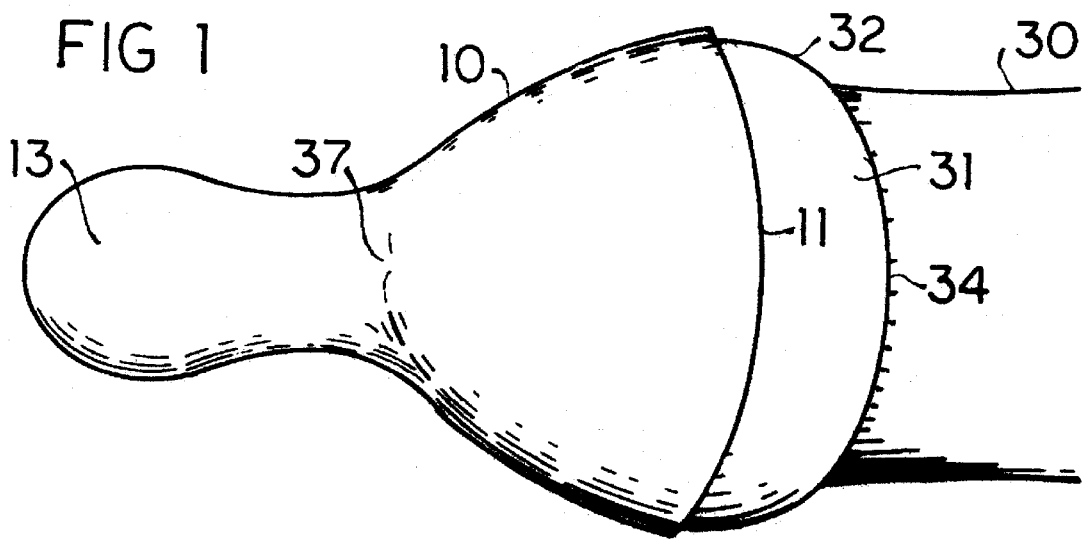
FIG. 1 is a plain elevational view taken from the top of a first preferred embodiment of the principles relating to the present invention shown attached to the glans penis.
Figure 2:
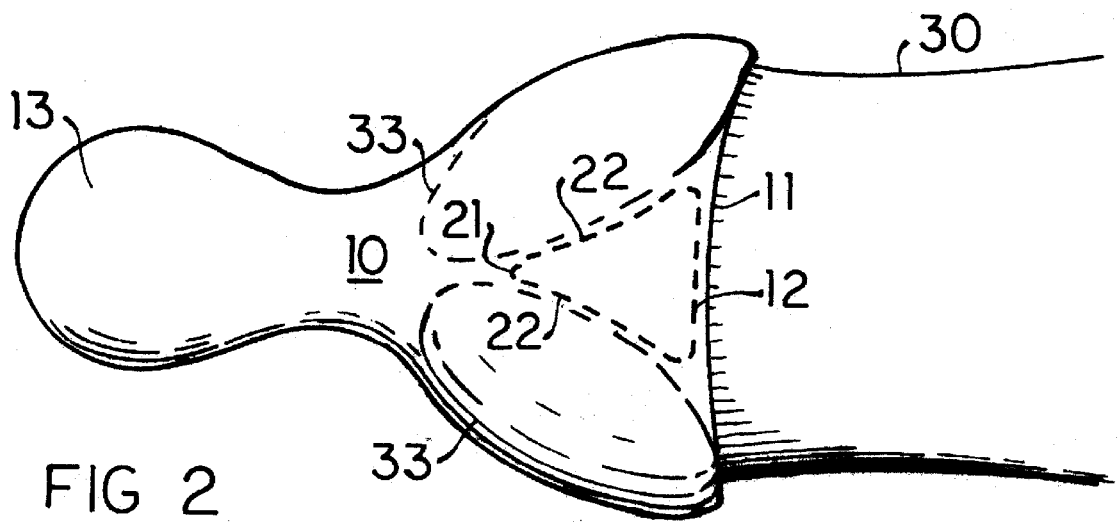
FIG. 2 is a plain elevational view taken from the bottom of a first preferred embodiment of the principles relating to the present invention shown attached to the glans penis.

An abbreviated condom 10 comprising a first preferred embodiment of the principles relating to the present invention is seen in FIGS. 1 & 2 attached to a forward portion of the head, i.e. the glans penis 31, of a tumescent penis 30. The rearward edge of the corona 32 and the rearward portion of the glans penis 31 are both uncovered and clearly exposed. The ventral portion of the glans penis 31 including the bilaterally symmetric lobes 33 is covered and the cleft therebetween is bridged with an interiorly projecting wedge structure 12 indicated with dotted lines in FIG. 2 and more clearly in FIGS. 3 & 4. The condom 10 is further seen in FIGS. 1 & 2 to possess a circumferential edge 11 which is substantially vertical in the orientation utilized, wherein the urethra is taken for a substantively horizontal axis, and which hence traverses the corona 32 which has a rearward incline upward of about forty-five degrees. A elongated tip expansible reservoir 13 is also seen extending forward of the urethra opening 37 as indicated in FIG. 1.

The condom is attached to the glans penis 31 as shown in FIG. 1 by means of an adhesive layer 14 which, as shown in FIGS. 3 & 4, is preferably covered by a removable backing 15 which further preferably and as shown comprises a strip with a tab 16 which protrudes from the circumferential edge 11 of the condom 10 during disposition or location upon the glans penis 31 and which is pulled away when the condom 10 is correctly positioned thereby exposing the adhesive layer 14. The adhesive layer 14 in this preferred embodiment comprises a circumferential band proximate the circumferential edge 11 of the condom 10.

The adhesive layer 14 preferably completes a circumference about the penis 30 in order to provide an effective seal against leakage of seminal fluid. It is not considered necessary that this adhesive layer 14 be confined to a narrow band, however, particularly in an embodiment such as that depicted in FIGS. 1–4 which both possesses an expansible reservoir 13 located forward of the urethra opening 37 and is also comparatively short. In this case an adhesive layer 14 may be applied to nearly the entire interior surface 17 of the condom excluding only the expansible reservoir 13 and the area immediately proximate the orifice 27 providing passage of the seminal fluid to the expansible reservoir 13.

It is considered necessary, however, to provide an interior surface 17 which will conform in use to the actual anatomy involved, particularly with regard to the cleft between the bilaterally symmetric lobes 33 of the glans penis 31 which, as seen in FIG. 2, each present a convex surface that is medially joined in the substantive merging of the two lobes 33. A congruent structure is utilized in which two interiorly projecting surfaces 27 diverge outwardly from a frontal medial apex 21 in a V configuration as seen in FIGS. 2–4 which enables the desired conformance to the anatomy concerned. Each of the two interiorly projecting surfaces 27 is preferably concave in order to conform to the convex surfaces presented by the two lobes 33 of the glans penis 31 while the interior projection effected accommodates the difference in elevation between the glans penis 31 and the cleft. An effective sealing of the condom 10 is thus enabled with use of an adhesive, preferably medical grade, layer 14 as described above.

Figure 5:
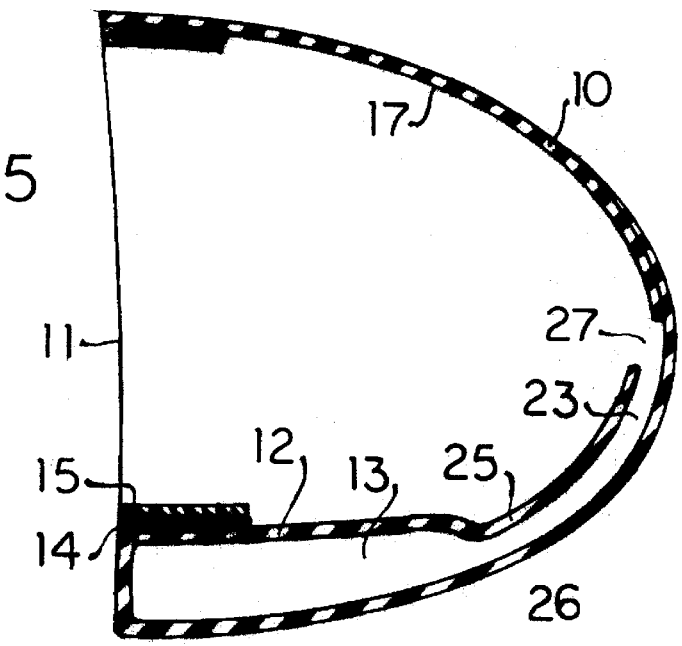
FIG. 5 is a cross sectional view depicting a second preferred embodiment of the principles relating to the present invention.

As clearly seen in FIG. 4, the interiorly projecting wedge structure 12 utilized in the embodiment of the principles relating to the present invention depicted in FIGS. 1–4 is essentially solid. In contrast, the interiorly projecting wedge structure 12 utilized in the embodiment of the principles relating to the present invention depicted in FIG. 5 is hollow, possesses a second wall 26 defining both an expansible reservoir 13 and an enclosed passageway 23 from an orifice 27 through the primary wall 25 which facilitates conveyance of seminal fluid to the expansible reservoir 13. It is also observed that the overall length of the abbreviated condom 10 in accordance with the principles relating to the present invention depicted in FIG. 5 is similar to that depicted in FIGS. 1–4 and still does not reach the dorsal rear edge 34 of the corona 32.

Figure 6:
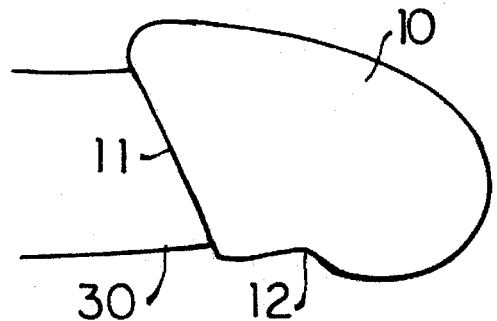
FIG. 6 is a plain elevational view taken from the side of a third preferred embodiment of the principles relating to the present invention shown attached to the glans penis.
Figure 7:
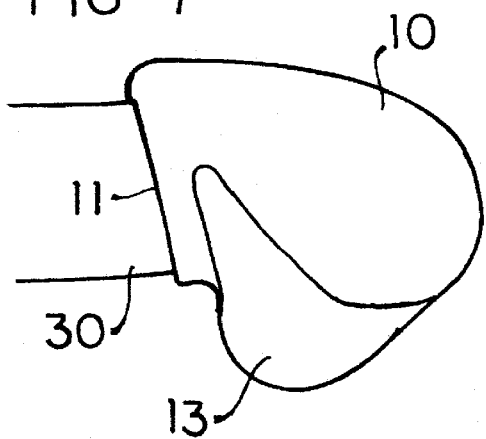
FIG. 7 is a plain elevational view taken from the side of a third preferred embodiment of the principles relating to the present invention shown attached to the glans penis after ejaculation.

The length of an abbreviated condom 10 in accordance with the principles relating to the present invention may reach beyond the dorsal rear edge 34 of the corona 32 as seen in FIGS. 6 & 7, in which case it is preferred that the contour defined by the entire corona 32 of the glans penis 31 be reflected in the structure of the condom 10. It is also considered in this case that an adhesive layer 14 is not considered necessary, particularly if the circumferential edge 11, which is immediately behind the dorsal rear edge 34 of the corona 32, is elastic and is given an increased wall thickness. An expansible reservoir 13 may be provided in the area behind the corona 32, largely upon the ventral side, as seen in FIG. 7.

The interiorly projecting wedge structure 12 provides conformance with the bilaterally symmetric lobes 33 and the cleft therebetween, as seen in FIG. 6, which facilitates intuitively correct positioning and ensures maintenance of the abbreviated condom 10 during use. A reduced differential wall thickness is suggested whereby the expansible reservoir 13 depicted in FIG. 7 is provided, which as mentioned above, is largely ventral in being located between the corona 32 and the circumferential edge 11 which is preferably thickened to provide an elastic band which snugly fits into the sulcus immediately behind the corona 32 or possesses a layer of adhesive 14 upon the interior surface 17 disposed in a band adjacent the circumferential edge 11. The use of a thinner wall structure in this area provides the expansible reservoir 13 depicted and also yields greater sensitivity during use to the ventral area of the penis 30 immediately behind and inclusive of the cleft which is considered particularly sensitive.

With regard to manufacture of an abbreviated condom in accordance with the principles relating to the present invention it is considered that either an injection molding or a dip molding similar to the manufacture of conventional full length condoms is considered suitable. In the latter case, however, a mold which is anatomically accurate with regard to the glans penis 31 is necessary. In either case the mold must have a surface which accurately reflects the bilaterally symmetric lobes 33 of the glans penis 31 which produces during molding an interior surface 17 possessing the interiorly projecting wedge structure 12 which fits snugly between and behind said lobes 33 and effectively bridges the cleft. Elastomeric material such as latex is recommended in all cases.

It has been mentioned that if an adhesive layer 14 is utilized, as recommended, a medical grade adhesive is further specifically suggested. With regard to the material favored for construction of the abbreviated condom 10 latex of a type used in manufacture of conventional full length condoms is considered wholly satisfactory. It is further noted that if differential wall thicknesses are desired injection molding will readily enable the same while dip molding using an anatomically accurate mold is suited to a substantially uniform wall thickness. In either case a generally thicker sheath wall thickness than that used in construction of a conventional full length condom bay be employed except in an area intended to provide an expansible reservoir 13. The use of a thicker sheath wall thickness will, of course, minimize the chance of accidental breakage.

The foregoing is intended to provide one practiced in the art with a detailed description of what is considered to be the best manner of making and using an embodiment in accordance with the principles relating to the present invention and is not to be interpreted as restrictive in any manner of the scope of the invention or the rights and privileges secured by Letters Patent protecting the same for which I claim:

1. An abbreviated condom intended to prevent the transmission of seminal fluid but leaving the shaft of a penis largely uncovered during use for greater sensitivity, said abbreviated condom comprising:

a thin walled sheath possessing a forward end and an opposed circumferential edge of appropriate size and shape to fit snugly about the glans penis possessing a substantially continuous uninterrupted interior surface and including an interiorly projecting wedge structure possessing a pair of interiorly projecting concave surfaces diverging laterally from a common medial apex in a direction away from said forward end which possesses an orifice providing a passageway to an expansible reservoir capable of containing the seminal fluid resulting from ejaculation.

2. The abbreviated condom of claim 1 wherein said circumferential edge possesses an increased wall thickness and is a distance away from said forward end sufficient to permit covering of the entire glans penis.

3. The abbreviated condom of claim 1 wherein said circumferential edge possesses a structure which conforms to the dorsal portion of the glans penis and an area behind the ventral portion of the glans penis.

4. The abbreviated condom of claim 3 wherein the distance between said circumferential edge and said forward end is less than the distance between the rear edge of the corona and the frontal opening of the urethra.

5. The abbreviated condom of claim 1 wherein said expansible reservoir is located upon said forward end.

6. The abbreviated condom of claim 5 wherein said expansible reservoir is comprised of an elongated extension of said thin walled sheath.

7. The abbreviated condom of claim 6 wherein said expansible reservoir is comprised of an elongated extension of said thin walled sheath located directly forward of said orifice.

8. The abbreviated condom of claim 1 wherein said expansible reservoir is comprised of a hollow within said wedge structure bounded by said thin walled sheath between adjacent primary and secondary walls and covering said orifice.

9. The abbreviated condom of claim 1 wherein said expansible reservoir is comprised of an area of said thin walled sheath which possesses a reduced differential wall thickness.

10. The abbreviated condom of claim 1 further possessing a layer of adhesive disposed upon said interior surface.

11. The abbreviated condom of claim 10 further possessing a removable backing for said layer of adhesive disposed upon said interior surface.

12. The abbreviated condom of claim 11 wherein said removable backing for said layer of adhesive disposed upon said interior surface further possesses a tab extending outward from said circumferential edge facilitating removal after disposition of the condom upon a penis.

13. The abbreviated condom of claim 12 wherein said layer of adhesive disposed upon said interior surface comprises a circumferential band.

14. The abbreviated condom of claim 13 wherein said layer of adhesive disposed upon said interior surface comprises a circumferential band located adjacent said circumferential edge.

15. The abbreviated condom of claim 14 further possessing a removable backing for said layer of adhesive disposed upon said interior surface comprising a circumferential band located adjacent said circumferential edge.

16. The abbreviated condom of claim 15 wherein said removable backing for said layer of adhesive disposed upon said interior surface further possesses a tab extending outward from said circumferential edge facilitating removal after disposition of said condom.

17. An abbreviated condom intended to prevent the transmission of seminal fluid but leaving the shaft of a penis largely uncovered during use for greater sensitivity, said abbreviated condom comprising:

a thin walled sheath possessing a forward end and an opposed circumferential edge of appropriate size and shape to fit snugly about the glans penis possessing a substantially continuous uninterrupted interior surface and including an interiorly projecting wedge structure possessing a pair of interiorly projecting surfaces diverging laterally from a common medial apex in a direction away from said forward end which possesses an orifice providing a passageway to an expansible reservoir located largely behind said interiorly projecting wedge structure capable of containing the seminal fluid resulting from ejaculation.

18. The abbreviated condom of claim 17 including an enclosed passageway between said orifice and said expansible reservoir located largely behind said interiorly projecting wedge structure.

19. An abbreviated condom intended to prevent the transmission of seminal fluid but leaving the shaft of a penis largely uncovered during use for greater sensitivity, said abbreviated condom comprising:

a thin walled sheath possessing a forward end and an opposed circumferential edge of appropriate size and shape to fit snugly about the glans penis possessing a substantially continuous uninterrupted interior surface and including an interiorly projecting wedge structure possessing a pair of interiorly projecting surfaces diverging laterally from a common medial apex in a direction away from said forward end which possesses an orifice providing a passageway to an expansible reservoir comprised of an area of said thin walled sheath which possesses a reduced differential wall thickness located largely behind said interiorly projecting wedge structure capable of containing the seminal fluid resulting from ejaculation.

\* \* \* \* \*